United States Patent [19]

Rosenthal

[11] 4,095,105

[45] June 13, 1978

[54] STANDARDIZING TEST SAMPLE

[75] Inventor: Robert D. Rosenthal, Gaithersburg, Md.

[73] Assignee: Neotec Corporation, Silver Spring, Md.

[21] Appl. No.: 765,308

[22] Filed: Feb. 3, 1977

[51] Int. Cl.² .................................................. G01J 1/00
[52] U.S. Cl. .................................... 250/338; 23/292; 73/1 R; 250/341; 252/408; 356/243
[58] Field of Search ............. 23/230 M, 292, 254 R, 23/254 US; 252/408; 210/198 C, 263; 356/243; 250/338, 341; 73/1 R

[56] References Cited

U.S. PATENT DOCUMENTS

| | | |
|---|---|---|
| 2,207,348 | 7/1940 | Jones et al. .................... 252/408 X |
| 3,205,355 | 9/1965 | Ehlert ............................ 356/243 X |
| 3,343,680 | 9/1967 | Rice et al. .......................... 210/263 |
| 3,478,210 | 11/1969 | Janacek ......................... 356/243 X |
| 3,861,788 | 1/1975 | Webster ............................. 350/315 |

*Primary Examiner*—Joseph Scovronek
*Attorney, Agent, or Firm*—Lane, Aitken, Dunner & Ziems

[57] ABSTRACT

In a sample used to test the accuracy of an instrument designed to quantitatively analyze organic material from the optical characteristics of the material, a sealed container is filled with a mixture of ground quartz and the organic material to be analyzed in the instrument. A window is provided in the sealed container to permit irradiation of the mixture so that the instrument can perform a quantitative analysis on the mixture in the sealed container.

12 Claims, 2 Drawing Figures

STANDARDIZING TEST SAMPLE

This invention relates to standard samples to check on the accuracy of instruments designed to quantitatively analyze grain samples.

In U.S. Pat. No. 3,861,788, issued Jan. 21, 1975, there is disclosed an instrument which analyzes grain samples by detecting the reflectivity or transmissivity of the samples at selected narrow band wavelengths. More specifically, the instrument disclosed in the above identified patent measures the percentage of oil, protein and water in each grain sample. In such a grain analyzing instrument as disclosed in the above described patent, it is important to be able to test the accuracy of the instrument. This testing can be done by means of a standard sample made of grain having known percentages of the constituents being measured.

A problem exists with the standard samples presently used because the moisture content in the grain of the samples is affected by the humidity of the atmosphere and the grain fails to maintain a constant percentage of its constituents. To overcome this problem, the grain of the samples is sealed in a container with epoxy or silicone grease so that the atmospheric environment cannot affect the grain. However, even these samples fail to maintain the accuracy of their readings after repeated use because when the sample is used to test the accuracy of an instrument, it is irradiated with light. This light causes moisture in the grain to migrate away from the irradiated area in the grain and thus causes the percentage of the constituents as measured by the instrument to change.

SUMMARY OF THE INVENTION

The present invention overcomes the problems of the prior art by providing a standard sample in which the moisture does not migrate in response to irradiation. In accordance with the present invention, the grain of the sample is mixed with a material, which is impervious to water. In addition, the water impervious material is transparent to the wavelengths which irradiate the same in the analyzer in which the standard sample is to be used. In the preferred embodiment, the material selected is ground quartz because quartz is essentially transparent in the near infrared light range in which the samples are irradiated by the analyzer of the above mentioned patent. Because the quartz is crystalline, it cannot absorb water or transmit water by capillary action. The mixture of quartz and grain has unique characteristics in that it has typical absorption points in the near infrared light range just as a pure grain sample has. This characteristic of the sample results because the quartz being transparent merely transmits the light until it hits a grain particle beneath it. Because the quartz is impervious to water, it tends to hold the moisture in position and resists the migration of the water away from the irradiated portion of the mixture. As a result, a standard sample comprising the mixture of the present invention in a sealed container will be uniquely stable and have constant reflectivity or transmissivity characteristics over a long period of time with repeated usage.

In accordance with a further feature of the present invention, a barrier of moisture absorbent salt is provided in the sample positioned to absorb any moisture which might leak into the sample. The salt barrier thus prevents moisture leakage from changing the moisture content of the sample.

DESCRIPTION OF THE PREFERRED EMBODIMENTS

Figure 1:
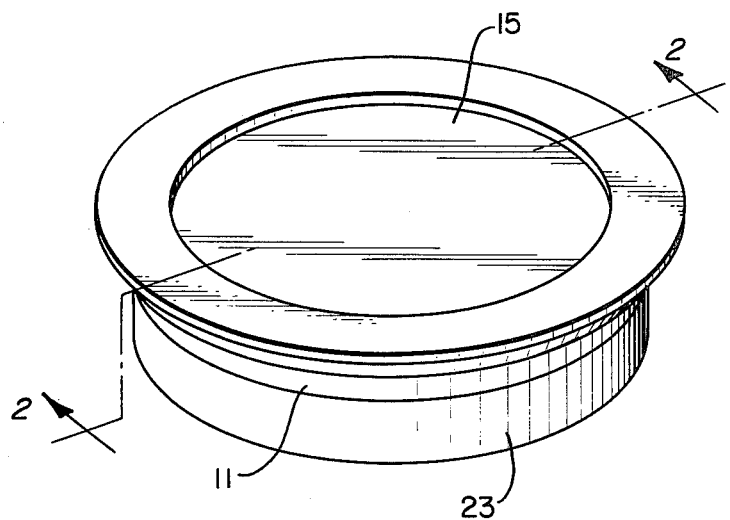
FIG. 1 is a perspective view of a sample containing the mixture of the present invention.
Figure 2:
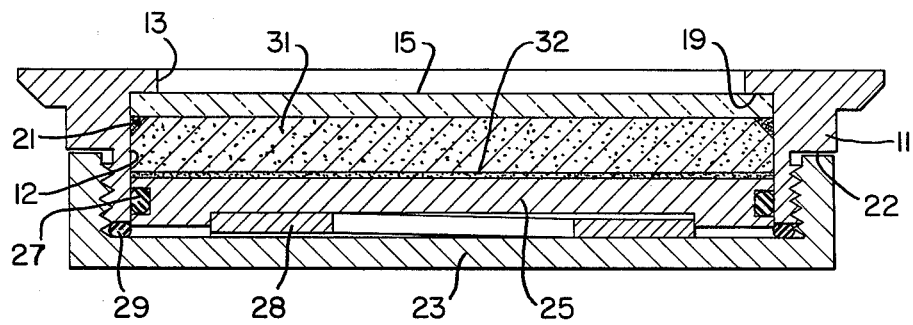
FIG. 2 is a sectional view taken along line 2—2 of FIG. 1.

As shown in FIGS. 1 and 2, the sample cup comprise a cylindrical container 11 defining a cylindrical cavit 12 and having an opening 13 at one axial end thereof. transparent pane 15 of glass or glass-like material i provided covering the opening 13 inside the containe 11. The opening 13 is circular and a little smaller i diameter than the cavity 12 and is coaxial therewitl The end of the container 11 at the opening 13 thu defines a shoulder 19 against which the pane 15 is posi tioned, the pane 15 extending across the entire cross sectional area of the cavity 12. The pane 15 is cemente in position by epoxy 21 around the edges thereof joinin the interior face of the pane to the sidewall of the cavit 12. The opposite end of the container 11 from the open ing 13 is of reduced diameter to define a shoulder 2 perpendicular to the axis of the cavity and is externall threaded to coact with complementary internal thread on a cap 23. A cylindrical piston member 25 is sized t make a sliding fit within the cavity 12. The outer cylin drical surface of the piston 25 is provided with a groov in which an O-ring 27 is positioned to make a seal witl the sidewall of the cavity. A wave washer or wav spring 28 is provided between the cap 23 and the pisto 25. An O-ring 29 is provided to fit within the cylindrica cavity defined by the cap 23 around the peripheral edg of the bottom of this cavity. This O-ring will be posi tioned between the end wall of the cap 21 and the axia end of the cylindrical sidewall of the container 11. Th standard sample mixture of the present invention desig nated by the reference number 31 is provided in th cavity 12 between the piston member 25 and the pan 15. Preferably a layer of moisture absorbent salt 32 i provided between the piston member 25 and the mix ture 31. The mixture 31 and the salt layer 32 fill th cavity 12 between the piston member 25 and the pan 15.

The mixture 31 comprises ground quartz and organi material of the type to be analyzed in the instrument fo which the standard sample is designed. As disclosed ii the above mentioned U.S. Pat. No. 3,861,788, the typ of organic material analyzed by the instrument is agri cultural products. An example of the organic material i grain such as wheat, which is preferably ground. Th ground quartz should be in the range of 25 to 75% b weight of the mixture. A preferred specific example o the mixture is with the ground quartz 50% by weight o the mixture with the remainder being the organic mate rial. The quartz is transparent in the infrared range ii which the sample is to be irradiated and is impervious t water.

In the manufacture of the sample, the pane 15 is ce mented to the container 11 and the cement is the cured. The organic material and the ground quartz ar thoroughly mixed together and the container 11 is posi tioned with the pane downwardly and is partly fille with the mixture of the ground quartz and grain. Th layer of moisture absorbent salt 32 is then added to th container covering the mixture of quartz and grain. Th piston 25 is then placed on top of the contents of th container 11 and the cap 23 is placed over the piston 25 and screwed onto the container 11. As the cap is screwed onto the container, the piston 25 is pushed down into the cavity 10 compressing the wave spring, the mixture of the organic material and the O-ring 29. The cap 23 is screwed onto the container 11 until a preselected gap remains between the axial end of the cylindrical sidewall of the cap 23 and the shoulder 22 on the container 11. The gap is selected so that the mixture of the quartz and organic material will be compressed precisely to the desired degree.

The resulting sample cup filled with the mixture constitutes the standard sample of the present invention having unique stability in its optical properties.

In use, the sample is placed in the instrument which is to be checked for accuracy such as the instrument described in the above mentioned patent. The instrument irradiates the mixture 31 with infrared light through the pane 12 and detects the resulting amplitude of the light reflected by the mixture 31. The irradiating light will be transmitted through the quartz of the mixture until it strikes a particle of the organic material and then be reflected because the quartz is transparent to the infrared light. Accordingly, the presence of the quartz in the mixture 31 does not affect the inherent optical property of the organic material of the mixture and the resulting reflectivity measurement is an accurate reflective measurement of the organic material contained in the mixture. The quartz, on the other hand, being impervious to water prevents the moisture in the mixture from migrating in the sample away from the infrared irradiation.

The sample described is a sample designed for an instrument which analyzes the samples by reflectivity. It will be apparent that the standards sample could be readily modified for use with an instrument which analyzes samples by transmissivity. Such a modified standard sample would contain the same mixture of quartz and organic material but the container of the mixture would be designed so that light could be transmitted through the mixture to a light detector.

Quartz is described as the material which is mixed with the organic material because it is transparent in the infrared range which is the preferred range for analysis of organic material and is the range used in the instrument in the above described patent. Other water impervious materials may be employed in the mixture with the organic material in place of the quartz. It is necessary that the material mixed with the organic material be impervious to water and transparent or light transmissive in the wavelength employed by the instrument for which the standard sample is designed. Accordingly, the water impervious material must be light transmissive in a wavelength band useful to analyze organic material by reflectivity or transmissivity.

Many other modifications may be made to the above described specific embodiment of the present invention without departing from the spirit and scope of the invention, which is defined in the appended claims.

I claim:

1. In a standard test sample comprising a closed container including a window transparent to irradiation of a predetermined wavelength, the improvement wherein a mixture of organic material and a second material is in said container positioned against said window, said second material being impervious to water and transparent to said predetermined wavelength, said organic material being present in an amount effective to be analyzed by irradiation, said second material being present in an amount effective to resist migration of moisture in said mixture.

2. A test sample as recited in claim 1, wherein said organic material is grain.

3. A test sample as recited in claim 1, wherein said wavelength is infrared and said second material is quartz.

4. A mixture as recited in claim 3, wherein said quartz is in the range of 25 to 75 percent by weight of said mixture.

5. A standard test sample as recited in claim 3, wherein said quartz is ground quartz.

6. A test sample as recited in claim 5, wherein said quartz is from 25 to 75 percent by weight of said mixture.

7. A test sample as recited in claim 5, wherein said organic material is grain.

8. A test sample as recited in claim 1, wherein said mixture is compressed against said window.

9. A mixture comprising particulate organic material and ground quartz, said organic material consisting of an agricultural product and being present in an amount effective to be analyzed by infrared irradiation, said ground quartz being present in an amount effective to restrict migration of moisture in said mixture.

10. A mixture as recited in claim 9, wherein said ground quartz is in the range of 25 to 75 percent by weight of said mixture.

11. A mixture as recited in claim 9, wherein said organic material is grain.

12. A mixture as recited in claim 11, wherein said grain is ground.

* * * * *